United States Patent [19]
Carson et al.

[11] Patent Number: 5,126,025
[45] Date of Patent: * Jun. 30, 1992

[54] METHOD AND APPARATUS FOR EFFECTING CAPILLARY ELECTROPHORESIS FRACTION COLLECTION ON A MEMBRANE

[75] Inventors: William W. Carson, Hopkinton; Yung-Fong Cheng, Milford; Martin Fuchs, Uxbridge, all of Mass.

[73] Assignee: Millipore Corporation, Bedford, Mass.

[*] Notice: The portion of the term of this patent subsequent to Jun. 9, 2009 has been disclaimed.

[21] Appl. No.: 575,111

[22] Filed: Aug. 30, 1990

[51] Int. Cl.⁵ ............... B01D 57/02; B01D 61/42; C25B 7/00; C25D 13/00
[52] U.S. Cl. ............... 204/180.1; 204/299 R; 204/182.3
[58] Field of Search ............ 204/182.8, 299 R, 180.1

[56] References Cited

U.S. PATENT DOCUMENTS

| | | | |
|---|---|---|---|
| 4,455,370 | 6/1984 | Bartelsman | 204/403 |
| 4,622,124 | 11/1986 | Kreisher | 204/182.8 |
| 4,631,120 | 12/1986 | Pohl | 204/182.8 |
| 4,631,122 | 12/1986 | Pohl | 204/182.8 |
| 4,936,974 | 6/1990 | Rose | 204/299 R |

*Primary Examiner*—John Niebling
*Assistant Examiner*—Caroline Koestner
*Attorney, Agent, or Firm*—Andrew T. Karnakis; Paul J. Cook

[57] ABSTRACT

A sample is injected into a capillary tube of a capillary electrophoresis apparatus. A sample solute on a porous layer is positioned in contact with an entrance end of the capillary tube and electrodes are positioned at the entrance end and exit end of the tube. The separated sample is collected at the exit end of the tube.

12 Claims, 3 Drawing Sheets

METHOD AND APPARATUS FOR EFFECTING CAPILLARY ELECTROPHORESIS FRACTION COLLECTION ON A MEMBRANE

BACKGROUND OF THE INVENTION

This invention relates to a method and apparatus for capillary electrophoresis with fraction collection onto a porous substrate. More particularly, this invention relates to an improved method and apparatus for capillary electrophoresis that permits isolation of solutes from a solution onto a porous substrate after separating the solutes by capillary electrophoresis.

Capillary electrophoresis (CE) is an efficient analytical separation technique for analysis of minute amounts of sample. CE separations are performed in a narrow diameter capillary tube, which is filled with an electrically conductive medium termed the "carrier electrolyte." An electric field is applied between the two ends of the capillary tube, and species in the sample move from one electrode toward the other electrode at a rate which is dependent on the electrophoretic mobility of each species as well as on the rate of bulk fluid movement in the tube. CE may be performed using gels or liquids in the capillary. In one liquid mode, known as free zone electrophoresis separations are based on differences in the free solution mobility of sample species. In another liquid mode, micelles are used to effect separations based on differences in hydrophobicity. This is known as Micellar Electrokinetic Capillary Chromatography. In capillary gel electrophoresi the capillary tube is filled with an electrically conductive gel rather than with liquid electrolyte. The gel functions as an anticonvective support to minimize sample band spreading. In free zone capillary electrophoresis, a high molecular weight solute such as a polyethylene oxide or hydroxymethyl cellulose can be added to the solvent to provide seiving effects analagous to that supplied by a gel.

CE is advantageous for several reasons. These include fast separation speed, high resolution and small sample size. For example, separation speeds using CE can be 10 to 20 times faster than conventional gel electrophoresis. In part, high resolution can be obtained through the use of high voltages because of the rapid dissipation of heat by the capillary. Further, band broadening due to convection is minimized due to the narrow capillary inner diameter. In most forms of CE, the lack of an anticonvective gel medium eliminates variable sample path tortuosity as a band spreading cause. In electrophoresis, the phenomenon of electroosmosis, or electroosmotic flow (EOF) occurs. This is a bulk flow of liquid which can move in either direction within the capillary tube and which affects all of the sample molecules regardless of charge. EOF ca contribute to improved resolution or separation speed in free-zone CE.

At the present time, fraction collection for CE is generally effected by inserting the exit end of the capillary tube into a vial containing electrolyte solution. An electrode is also inserted into the vial and the separation voltage is activated to effect migration of the solute from the capillary into the vial. After a period of time, the capillary tube end is moved to another vial and the process is repeated. This process is undesirable since the sample becomes diluted by the electrolyte in the vial. In addition, it is difficult to determine when to transfer the capillary exit end to another vial since, in general, one is not able to monitor when a sample portion has completely exited the capillary tube, particularly when the sample bands are closely spaced. One approach for overcoming this problem was reported by Huang and Zare at the High Performance Capillary Electrophoresis Symposium in January, 1990. The capillary is modified adjacent to the exit end by forming a hole in the capillary wall, making a porous frit in the hole and surrounding the porous frit with a reservoir filled with electrolyte. Electrical contact is made to the capillary through the fritted hole by means of an electrode in the reservoir filled with electrolyte. The exit en of the capillary is contacted with a rotating drum covered with filter paper. Most of the liquid in the Capillary is carried past the porous frit by electroosmotic flow onto the filter paper. This approach is undesirable since it is difficult and time consuming to construct the fritted hole. Also, a portion of the sample is lost from the capillary through the frit and into the reservoir. Also, this technique only function when an electrosmotic flow occurs toward the capillary exit.

U.S. Pat. Nos. 4,631,120 and 4,631,122 disclose a method and apparatus for effecting electrophoresis through a porous substance such as a gel or paper. The porous substance rather than a liquid is required as an anticonvective medium. In one mode, the porous substance is positioned vertically and wherein one liquid electrolyte reservoir is positioned above the porous substance and a second liquid electrolyte reservoir is positioned below the porous substance. In a second configuration the porous substance is positioned horizontally in a open slot. This method does not permit the use of a liquid transport medium since the medium would become admixed with the electrolytes within which the electrodes are immersed. The disadvantages of this method and apparatus are the same as that encountered in gel electrophoresis not utilizing a capillary, namely; poor rejection of heat generated during the electrophoresis process, slow rate of separation spreading, band spreading caused by differential tortuous paths for the sample within the gel and the requirement of manual sample loading. In addition, in both cases the end of the transport medium is immersed in an electrolyte and a portion of the sample migrating to the collection membrane can be lost in the electrolyte. In addition, the detection mean is off line and usually is nonquantitative.

U.S. Pat. No. 4,735,697 disclose a method and apparatus for separating complex mixtures of biomolecules such as proteins or nucleic acids in two stages. In the first stage, the mixture is separated by high performance liquid chromatography (HPLC). The effluent from the HPLC stage is treated so that the components exhibit a uniform surface charge such as by contact with a detergent. The treated HPLC effluent then is deposited on the surface of an electrically charged separation gel. This system does not permit high resolution spatial collection of sample since the electric field within the separation gel is not focussed at the HPLC column exit.

Western blotting is a technique by which samples separated in a gel during a prior electrophoresis step are transferred to a membrane. The membrane and gel are positioned between two plate electrodes and the membrane is wet with an electrolyte such as with a wet absorbent layer positioned in contact with the membrane. The samples in the gel are caused to migrate to the membrane by the voltage applied between the plate electrodes.

It would be desirable to provide a means for recovering separated samples from a capillary electrophoresis process which does not dilute the sample and which avoids sample loss. In addition it would be desirable to provide such a means which is simple to produce and operate. It would also be desirable to provide a means for collecting a sample in a format which is compatible with present analysis techniques, such as amino acid sequencing, radio immuno assay, ELISA or the like. It would also be desirable to provide a means that preserves the spatial resolution of the CE process in the recovered separated sample species.

SUMMARY OF THE INVENTION

The present invention provides a CE collection process and apparatus which permits the use of CE using any presently available CE transport medium including liquids or gels to analyze samples and which permits the collection of separated samples on a porous substrate in higher concentration than with present collection techniques. An electrode structure is provided comprising an electrically conductive solid surface which can be a nonporous surface or a porous surface such as a screen, a porous substrate wetted with an aqueous or nonaqueous electrolyte solution positioned in contact with the solid surface, and the exit end of an electrophoresis capillary in contact with the porous substrate. An absorbent layer wetted with a conductive electrolyte solution can be interposed between the porous substrate and the conductive means to provide a source of ions in solution to the porous substrate. Alternatively an ion containing solution can be applied directly to the porous substrate by any convenient means such as by spraying. Means are provided for effecting an electrical voltage between the electrically conductive solid surface and a second electrode at or adjacent to the entrance end of the capillary. In use, the electrode structure is positioned at the exit end of a capillary electrophoresis tube. The electrode structure of this invention replaces the presently used vessel containing carrier electrolyte solution in which the capillary tube exit is immersed. The entrance end of the capillary electrophoresis tube generally is positioned within a vessel containing an electrolyte solution as well as the second electrode. To perform a CE analysis, a volume of sample is introduced into the capillary entrance. This is accomplished by moving the entrance end of the capillary into a vessel containing the sample solution and then using differential or hydrostatic pressure or an electric field created by an electrode in contact with the sample solution to drive sample molecules into the capillary. The entrance end is then returned to the vessel containing electrolyte solution and the second electrode, and a high voltage is applied from the second electrode in the vessel at the entrance end of the capillary to the electrode structure positioned at the exit end of the capillary. The sample molecules migrate through the capillary tube under the influence of the electric field created by the voltage applied to the electrodes. Upon exiting the capillary tube, sample is retained on the porous substrate portion of the electrode structure. By utilizing this invention, the entire sample can be recovered after capillary electrophoresis since it is deposited directly on the porous substrate while avoiding an environment where sample loss can occur. In addition, since the sample is deposited on the porous substrate, it is in a form which permits further analysis by a wide variety of presently available techniques including amino acid sequencing, radioimmunoassay, ELISA, hydrolysis followed by composition analysis, chemoluminescence, enzymatic digestion, bioassays or the like.

DESCRIPTION OF SPECIFIC EMBODIMENTS

Figure 1:
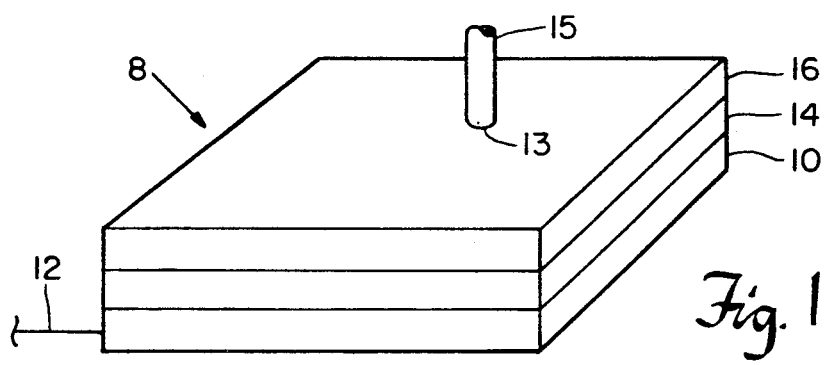
FIG. 1 is a perspective view of an electrode structure utilized in this invention.

The term "capillary tube" as used herein means a tube having an inner diameter between about 1 and 500 micrometers.

The apparatus of this invention comprises a capillary tube having an entrance end and an exit end. Electrodes are positioned adjacent to each end of the capillary tube. In order to collect solute sample introduced into and passed through the capillary tube, an electrode structure at the exit end is provided which includes a porous layer adapted to retain the solute sample and to permit passage of the solvent for the sample through the porous layer. The electrode at the exit end comprises an electrically conductive layer electrically connected to a source of electrical energy and the porous layer which is positioned between the electrically conductive layer and the exit end of the capillary tube. The porous layer can directly contact the conductive layer or can be electrically connected to the conductive layer such as by a salt bridge or by a solution of electrolyte. In an alternative embodiment, an absorbent layer containing an electrolyte solution is interposed between the conductive layer and the porous layer utilized to retain the sample solute. The absorbent layer provides a source of aqueous or nonaqueous electrolyte to the porous layer thereby to provide a conductive bridge between the conductive layer and the exit end of the capillary tube. The absorbent layer can comprise an ultrafiltration or micropoous membrane, filter paper, fiber glass, woven fabric or the like so long as the material is capable of absorbing the electrolyte so as to provide a source of electrolyte to the porous layer to maintain electrical conductivity therein while collecting the sample.

The porous layer comprises a hydrophilic or hydrophobic, microporous or ultrafiltration membrane or can comprise a gel such as a polyacrylamide or aqueous gel membrane. It can be advantageous to utilize a membrane which is hydrophobic when it is dry and which can be wet to become capable of transporting aqueous liquid through its thickness since these membranes can bind molecules such as proteins. Alternatively preferred membranes for binding proteins include hydrophilic polyamides or nitrocellulose. Generally, for use with aqueous electrolytes the hydrophobic membranes can be wet by contacting the membrane with a water miscible organic solvent such as ethanol, methanol, acetone, acetonitrile or the like and subsequently contacting the membrane with as aqueous liquid. Representative membranes include those formed from polyolefins such as polyethylene, polypropylene, polymethylpentene, or the like; polystyrene or substituted polystyrenes; fluorinated polymers including poly(tetrafluoroethylene), polyvinylidene fluoride or the like; polysulfones such as polysulfone, polyethersulfone or the like; polyesters including polyethylene terephthalate, polybutylene terephthalate or the like; polyacrylates or an polycarbonates; polyamide nitrocellulose, vinyl polymers such as polyvinyl chloride and polyacrylonitriles. Copolymers also can be employed such a copolymers of butadiene and styrene, fluorinated ethylene-propylene copolymer, ethylene-chlorotri-fluoroethylene copolymer or the like. Generally, the microporous membrane has an average pore size between about 0.001 and 10 microns and more usually between about 0.1 to 5.0 microns. Ultrafiltration membranes comprise membranes having a relatively open porous substructure and a thin skin having small pores as is well known in the art.

The conductive layer can comprise a nonporous or porous solid layer such as a screen formed from a metal or conductive graphite or carbon or the like.

Referring to FIG. 1, the electrode structure utilized in this invention to collect sample is shown. The electrode structure 8 comprises an electrically conductive plate 10 connected to an electrical lead 12, a liquid absorbent layer 14 and a porous layer adopted to retain solute sample 16. The exit end 13 of capillary tube 15 contacts the porous layer 16. The absorbent layer 14 is held to the plate 10 by gravity. The absorbent layer is wet with a liquid containing an electrically conductive electrolyte. The porous layer 16 contacts the absorbent layer and is kept wet by the liquid in the absorbent layer.

Figure 2:
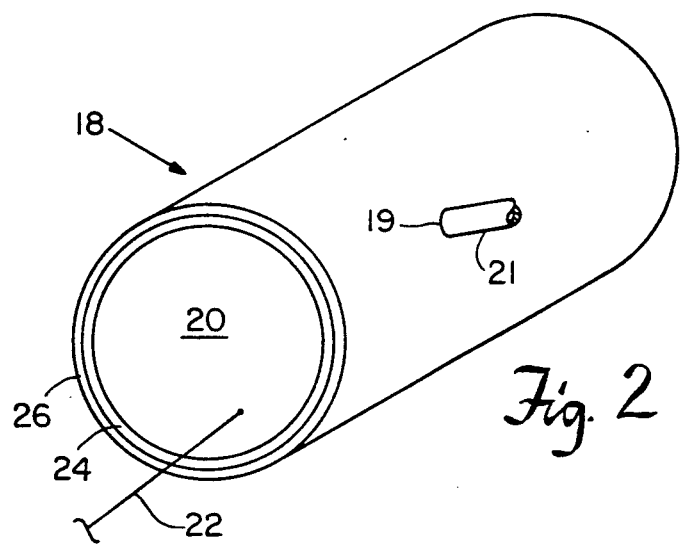
FIG. 2 is a perspective view of an alternative electrode structure utilized in this invention.

Referring to FIG. 2, the electrode structure 18 can be in the form of a cylinder and comprises a solid or hollow cylindrical electrically conductive plate 20 connected to electrical lead 22, absorbent layer 24 and porous layer 26. Porous layer 26 contacts the exit end 19 of capillary tube 21.

Figure 3:
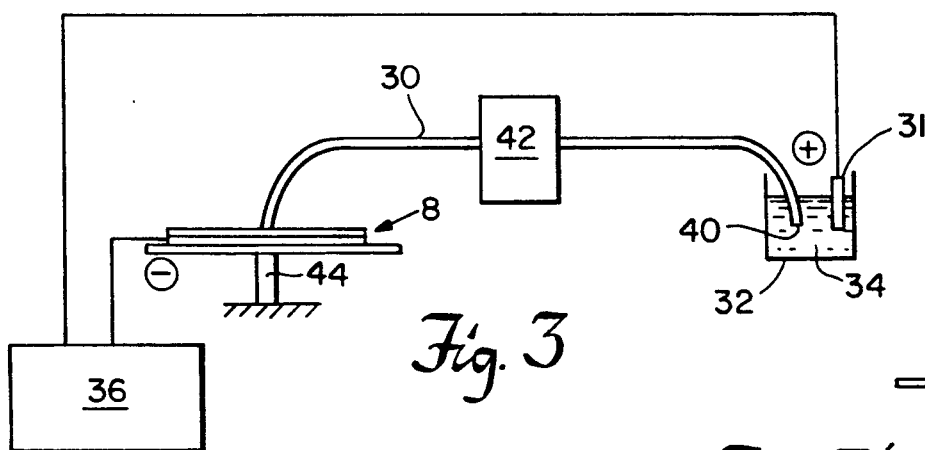
FIG. 3 is a schematic view of a capillary electrophoresis process utilizing this invention.
Figure 3A:
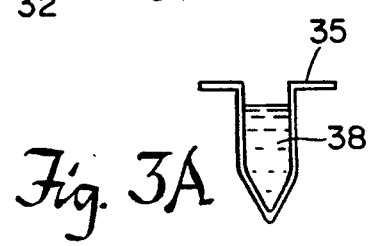
FIG. 3A is a vessel for introducing sample into the system of FIG. 3.

Referring to FIG. 3, a basic system that can be used in free zone capillary electrophoresis, capillary gel electrophoresis or micellar electrokinetic capillary chromatography is shown. As shown in FIG. 3, a capillary tube 30, is positioned in reservoir 32 which contains carrier electrolyte and with the other end in contact with the electrode structure 8. A voltage from power supply 36 is applied between electrode 31 in electrolyte reservoir 32 and electrode structure 8. The sample passes through the capillary tube 30, past detector 42, to electrode structure 8. The electrode structure 8 is placed upon support 44 which is capable of moving the electrode structure 8 translationally or rotationally so that a pattern of the separated sample is formed on the exposed surface of the porous layer. The flat electrode structure of FIG. 1 can be replaced with the cylindrical structure of FIG. 2 in which case the cylindrical structure is rotated and/or translated axially in contact with the exit end of the capillary tube 30. The detector 42 can be any detector capable of analyzing the sample such as a UV absorbance detector, a fluorescence detector, a conductivity detector or the like. To introduce sample into the capillary the entrance end 40 of capillary 30 and electrode 31 are placed into vessel 35 containing sample solution 38. The voltage is then applied to electrode 31 and electrode structure 8 for a brief period of time to drive sample into capillary entrance 40. Alternatively, hydrostatic or differential gas pressure can be applied to vessel 35 to force sample solution into capillary entrance 40.

Figure 5:
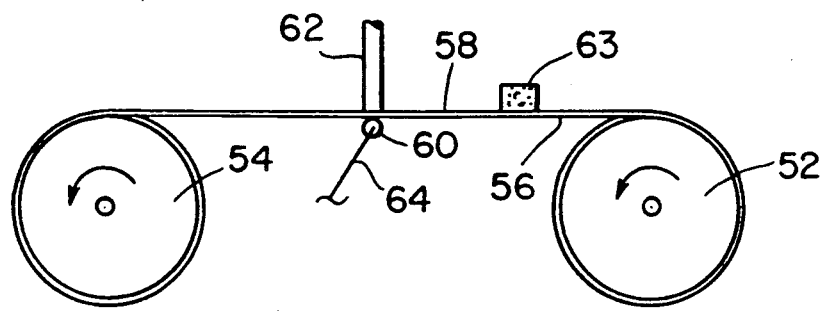
FIG. 5 is a schematic view of a capillary electrophoresis process of this invention utilizing a continuous porous substrate.

Referring to FIG. 5, an alternative process arrangement is shown. Feed roll 52 and take up roll 54 are utilized to move a metallized flexible layer 56 and membrane 58 between roller 60 and the exit end of capillary tube 62. Sponge 63 serves as a reservoir for aqueous electrolyte to effect wetting of membrane 58 and to provide an electrical connection between the roller 60 through electrical connector 64 and a solute reservoir (not shown) at the entrance end of the capillary as described above. Any means for wetting the membrane with an electrolyte can be employed including spraying means, contact with an electrolyte reservoir or the like.

Figure 6:
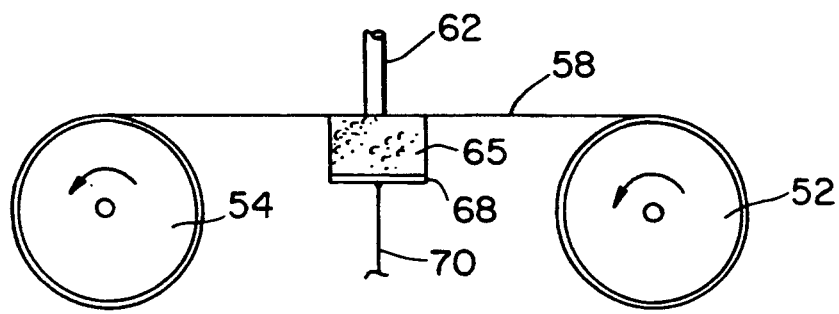
FIG. 6 is a schematic view of an alternative eletrophoresis process of this invention utilizing a continuous porous substrate.

Referring to FIG. 6, a membrane sheet 58 is passed from feed roll 52 to take-up roll 54 between capillary tube 62 and sponge 65 which is positioned on metal plate 68 connected to electrical lead 70. A voltage is applied through the capillary tube 62 in the manner described above.

Figure 7:
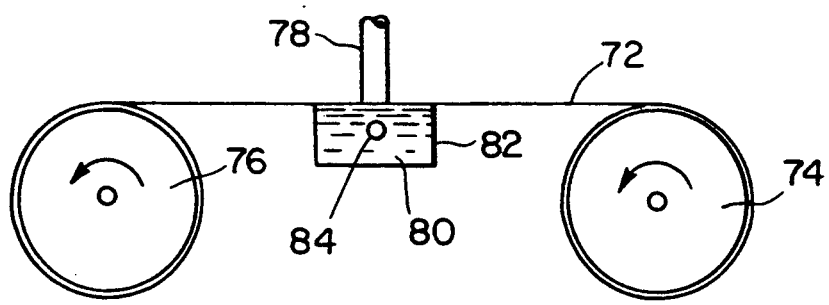
FIG. 7 is a schematic view of an alternative process of this invention utilizing a submerged electrode.

Referring to FIG. 7, a membrane sheet 72 is passed from feed roll 74 to take up roll 76 into contact with capillary tube 78 and electrolyte 80 in container 82 and electrode 84 is positioned within electrolyte 80. The sample exits from capillary tube 78 and is retained on membrane 72 in the manner described above.

Figure 8:
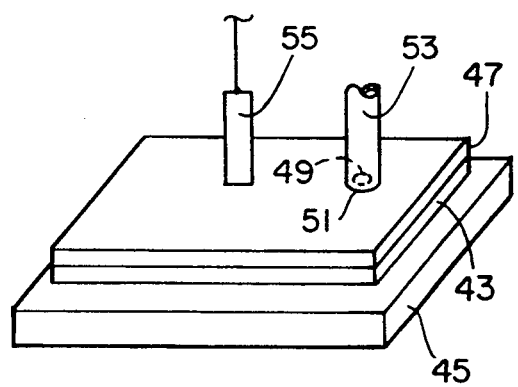
FIG. 8 is a schematic view of an alternative apparatus of this invention.

Referring to FIG. 8, an absorbent layer 43 containing an electrolyte is positioned on support 45. A membrane 47, wet with electrolyte is positioned on absorbent layer 43 and is in contact with exit end 51 of capillary 53 and also in contact with electrode 55.

Subsequent to depositing the sample on the membrane, the sample can be reacted with conventional reagents used in available assay or detection techniques. Examples of such reagents include radiolabeled or fluorescent labeled reagents such as antigens or antibodies; staining reagents such as Coomassie Blue, Amido Black, Silver Stain or Xylene Cyanide or orthophthaldehyde.

The following example illustrates the present invention and are not intended to limit the same.

EXAMPLE 1

For this experiment, the direct collection of eluent onto a continuously moving surface using the experimental apparatus shown in FIG. 3 was effected. The capillary had a 100 um i.d., 360 um o.d. and a length of 80 cm. A UV detector was employed at a wavelength of 210 nm. The detection region was 20 cm from the exit end of the capillary. The attenuation for this detector was adjusted to 0.05 AUFS. The strip chart recorder speed was set at 0.25 cm/min. The collection carousel comprising the flat electrode structure shown in FIG. 1 was spun at 2.254 RPH (Revolution Per Hour). The surface velocity was calculated to be 0.55 mm/min at 2.8 cm distance from the center of carousel.

A 1 mg/ml Myoglobin stock solution and a 1 mg/ml β-Lactoglobulin stock solution were prepared in 25 mM pH 7.14 phosphate buffer solution. Equal volumes of these two protein solutions were mixed prior to electrophoretic injection for CE.

Staining reagent was prepared by dissolving 1.25 g of Brilliant Blue R250 (Coomassie Brilliant Blue R, B 0630 Sigma) in 500 ml fixative solution (by combining 200 ml of methanol, 35 ml of glacial acetic acid, and 265 ml of reverse osmosis treated water). This solution was stored tightly capped in a brown bottle at room temperature. Coomassie Brilliant Blue forms electrostatic bonds with $NH^{+3}$ groups and non-covalent bonds with non-polar regions in the proteins. A 90% (v/v) Methanol solution was prepared in water as destaining solution.

A Polyvinylidene difluoride hydrophobic membrane (Immobilon-P available from Millipore Corporation, Bedford, Massachusetts) was employed as the fraction collection medium. Whatman filter paper (3MM Chr) was used as an absorbent layer between the membrane and a stainless steel electrode. The absorbent layer contained 25 mM pH 7.14 phosphate buffer and served as a buffer reservoir. The electrode structure was assembled as follows: first, 2 layers of Whatman filter papers were immersed in buffer solution; second, the wetted filter papers were assembled on top of steel electrode which also functioned as a rotation carousel; third, the immobilon-P was immersed in methanol for about 5 seconds and then immersed in buffer solution; fourth, the treated membrane was laid on the filter paper buffer reservoir in a manner to assure there was no air entrapped in the assembly; fifth, the assembled membrane collection apparatus was raised to contact the exit end of the capillary; sixth, sample solution was introduced into the entrance end of the capillary by electromigration from a non-conducting vial at 8 KV for 15 seconds; the sample vial was then replaced by another vial filled with buffer solution, and the voltage was applied at 18 KV to carry out electrophoretic separation for about 30 minutes; lastly, the membrane was stained in staining reagent for 15 minutes and destained in destaining solution twice. After staining with Coomassie Blue two elongated spots were visible; one for Myoglobin and the second for $\beta$-lactoglobulin. Each spot corresponded to a few tens of naograms of these proteins.

Additionally, the experiment was performed under regular CE conditions (having vials on both end of the capillary to form a complete circuit) without the fraction collection electrode structure.

Figure 4:
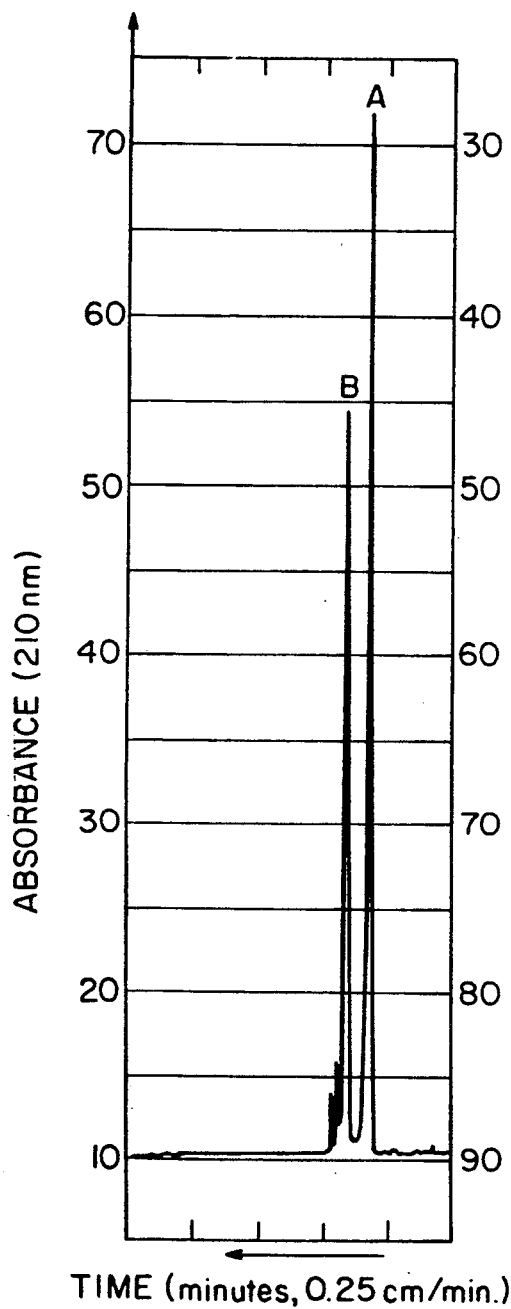
FIG. 4 is an electropherogram of a sample by the process of Example I.

FIG. 4 shows the electropherogram obtained from regular CE of an injection of two-component mixture containing Myoglobin (0.5 mg/ml) and $\beta$-Lactoglobulin (0.5 mg/ml). Peak A is Myoglobin and peak B is $\beta$-Lactoglobulin.

The observed current was stable at 96 uA during the electrophoretic separation in both regular CE, and membrane collection.

I claim:

1. Apparatus for collecting a sample which comprises:
   a. a capillary tube having an entrance end and an exit end, said entrance end adapted to be positioned within a liquid containing a sample solute,
   b. said capillary containing an electrically conductive composition adapted to permit sample passage therethrough,
   c. a first electrode adjacent said entrance end and beign in electrical contact with said electrically conductive composition within said capillary,
   d. said exit end being in contact with a porous layer adapted to retain said sample solute,
   e. said porous layer containing a liquid electrolyte,
   f. a second electrode being in electrical contact with said porous layer, and
   g. means for effecting an electrical voltage between said first electrode and said second electrode.

2. The apparatus of claim 1 wherein said porous layer is a microporous membrane.

3. The apparatus of claim 2 wherein said membrane is an ultrafiltration membrane.

4. The apparatus of any one of claims 1, 2 or 3 wherein said second electrode is a solid metal layer.

5. The apparatus of any one of claims 1, 2 or 3 wherein said second electrode is in electrical contact with said porous layer by means of a metal screen.

6. The apparatus of any one of claims 1, 2 or 3 wherein an absorbent layer wetted with an electrolyte is in contact with said porous layer.

7. The apparatus of claim 1 wherein said second electrode in graphite.

8. The process for effecting capillary electrophoresis which comprises; introducing a solute sample into an entrance end of a capillary tube containing an electrically conductive composition and having said entrance end and an exit end, applying an electrical voltage between a first electrode adjacent said entrance end and a second electrode adjacent said exit end and through said electrically conductive composition, passing said solute sample through said capillary tube under the influence of said electrical voltage, and depositing said solute sample on a porous layer adjacent said exit end, said porous layer being in electrical contact with said second electrode adjacent said exit end.

9. The process of claim 8 wherein said porous layer is moved relative to said exit end.

10. The process of claim 8 wherein said solute sample is detected within said capillary tube.

11. The process of claim 9 wherein said solute sample is detected within said capillary tube.

12. The apparatus of any one of claims 1, 2 or 3 including a second porous layer being in contact with said exit end.

* * * * *